United States Patent
Bechtel et al.

(10) Patent No.: US 11,642,230 B2
(45) Date of Patent: May 9, 2023

(54) EXPANDABLE INTERSPINOUS PROCESS FIXATION DEVICE

(71) Applicant: GLOBUS MEDICAL, INC., Audubon, PA (US)

(72) Inventors: Matthew Bechtel, Philadelphia, PA (US); Hilliary Kopp, Virginia Beach, VA (US)

(73) Assignee: Globus Medical, Inc., Audubon, PA (US)

( * ) Notice: Subject to any disclaimer, the term of this patent is extended or adjusted under 35 U.S.C. 154(b) by 50 days.

(21) Appl. No.: 17/177,671

(22) Filed: Feb. 17, 2021

(65) Prior Publication Data

US 2021/0169657 A1 Jun. 10, 2021

Related U.S. Application Data

(60) Continuation of application No. 15/920,708, filed on Mar. 14, 2018, now Pat. No. 10,945,858, which is a
(Continued)

(51) Int. Cl.
*A61F 2/44* (2006.01)
*A61F 2/30* (2006.01)
(Continued)

(52) U.S. Cl.
CPC .......... *A61F 2/447* (2013.01); *A61B 17/7068* (2013.01); *A61F 2/44* (2013.01); *A61F 2/442* (2013.01); *A61F 2/4455* (2013.01); *A61F 2/4611* (2013.01); *A61F 2002/30266* (2013.01); *A61F 2002/30387* (2013.01); *A61F 2002/30405* (2013.01); *A61F 2002/30411* (2013.01); *A61F 2002/30471* (2013.01); *A61F 2002/30482* (2013.01); *A61F 2002/30484* (2013.01); *A61F 2002/30517* (2013.01); *A61F 2002/30522* (2013.01); *A61F 2002/30523* (2013.01); *A61F 2002/30538* (2013.01); *A61F 2002/30556* (2013.01); *A61F 2002/30558* (2013.01); *A61F 2002/30579* (2013.01); *A61F 2002/30593* (2013.01); *A61F 2002/30601* (2013.01);
(Continued)

(58) Field of Classification Search
None
See application file for complete search history.

(56) References Cited

U.S. PATENT DOCUMENTS

| 4,349,921 A | 9/1982 | Kuntz |
| 4,599,086 A | 7/1986 | Doty |

(Continued)

FOREIGN PATENT DOCUMENTS

| CA | 2088066 A1 | 1/1992 |
| DE | 4012622 C1 | 7/1991 |

(Continued)

*Primary Examiner* — Tessa M Matthews

(57) ABSTRACT

An expandable interspinous process fixation system capable of restoring spinal stability and facilitating fusion. In one embodiment, the expandable interspinous process fixation system includes a central ramp, a first endplate, and a second endplate, the central ramp capable of being moved in a first direction to move the first and second endplates outwardly and into an expanded configuration. Each endplate supporting fixed and/or adjustable spinous process engaging plates.

20 Claims, 11 Drawing Sheets

Related U.S. Application Data continuation-in-part of application No. 15/662,423, filed on Jul. 28, 2017, now Pat. No. 10,512,550, which is a continuation-in-part of application No. 15/635,267, filed on Jun. 28, 2017, now Pat. No. 10,842,644, which is a continuation-in-part of application No. 15/189,188, filed on Jun. 22, 2016, now Pat. No. 10,085,849, which is a continuation-in-part of application No. 15/014,189, filed on Feb. 3, 2016, now Pat. No. 9,907,673, which is a continuation-in-part of application No. 14/109,429, filed on Dec. 17, 2013, now Pat. No. 9,370,434, which is a division of application No. 12/875,818, filed on Sep. 3, 2010, now Pat. No. 8,632,595.

(51) Int. Cl.
 A61F 2/46 (2006.01)
 A61B 17/70 (2006.01)

(52) U.S. Cl.
 CPC ......... *A61F 2002/30622* (2013.01); *A61F 2002/30841* (2013.01); *A61F 2002/30843* (2013.01); *A61F 2002/30904* (2013.01); *A61F 2220/0016* (2013.01); *A61F 2310/00011* (2013.01); *A61F 2310/00017* (2013.01); *A61F 2310/00023* (2013.01); *A61F 2310/00179* (2013.01)

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,062,375 A | 5/2000 | Pupp |
| 6,080,193 A | 6/2000 | Hochshuler |
| 6,099,531 A | 8/2000 | Bonutti |
| 6,126,689 A | 10/2000 | Brett |
| 6,137,405 A | 10/2000 | Carney |
| 6,176,882 B1 | 1/2001 | Biedermann |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,431,735 B2 | 10/2008 | Liu et al. |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,763,074 B2 | 7/2010 | Altarac et al. |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 8,123,810 B2 | 2/2012 | Gordon et al. |
| 8,647,386 B2 | 2/2014 | Gordon |
| 9,005,291 B2 | 4/2015 | Loebl et al. |
| 9,480,502 B2 * | 11/2016 | Whiton .......... A61B 17/7068 |
| 9,486,251 B2 * | 11/2016 | Zappacosta ...... A61B 17/7068 |
| 9,724,134 B2 * | 8/2017 | Zappacosta ...... A61B 17/7068 |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0153065 A1 | 8/2004 | Lim |
| 2005/0021041 A1 | 1/2005 | Michelson |
| 2005/0021145 A1 | 1/2005 | de Villiers |
| 2005/0033432 A1 | 2/2005 | Gordon |
| 2005/0080422 A1 | 4/2005 | Otte |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | McLuen |
| 2006/0149385 A1 | 7/2006 | McKay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 | 6/2008 | Olmos |
| 2008/0147194 A1 | 6/2008 | Grotz |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |

(56) References Cited

U.S. PATENT DOCUMENTS

| | | |
|---|---|---|
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy |
| 2009/0076616 A1 | 3/2009 | Duggal |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0226314 A1 | 9/2012 | Chin et al. |
| 2012/0265309 A1 | 10/2012 | Glerum |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158669 A1 | 6/2013 | Sungarian |
| 2013/0184754 A1 | 7/2013 | Taber et al. |
| 2014/0188170 A1 | 7/2014 | Zappacosta et al. |
| 2014/0343608 A1 | 11/2014 | Whiton et al. |
| 2015/0057755 A1 | 2/2015 | Suddaby et al. |
| 2015/0112437 A1 | 4/2015 | Davis et al. |
| 2020/0345634 A1* | 11/2020 | Mann .................. A61K 31/7036 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| FR | 2794968 | 12/2000 |
| JP | 2000-513263 | 10/2000 |
| JP | 2016533221 A | 10/2016 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |
| WO | 2013130907 A1 | 9/2013 |

* cited by examiner

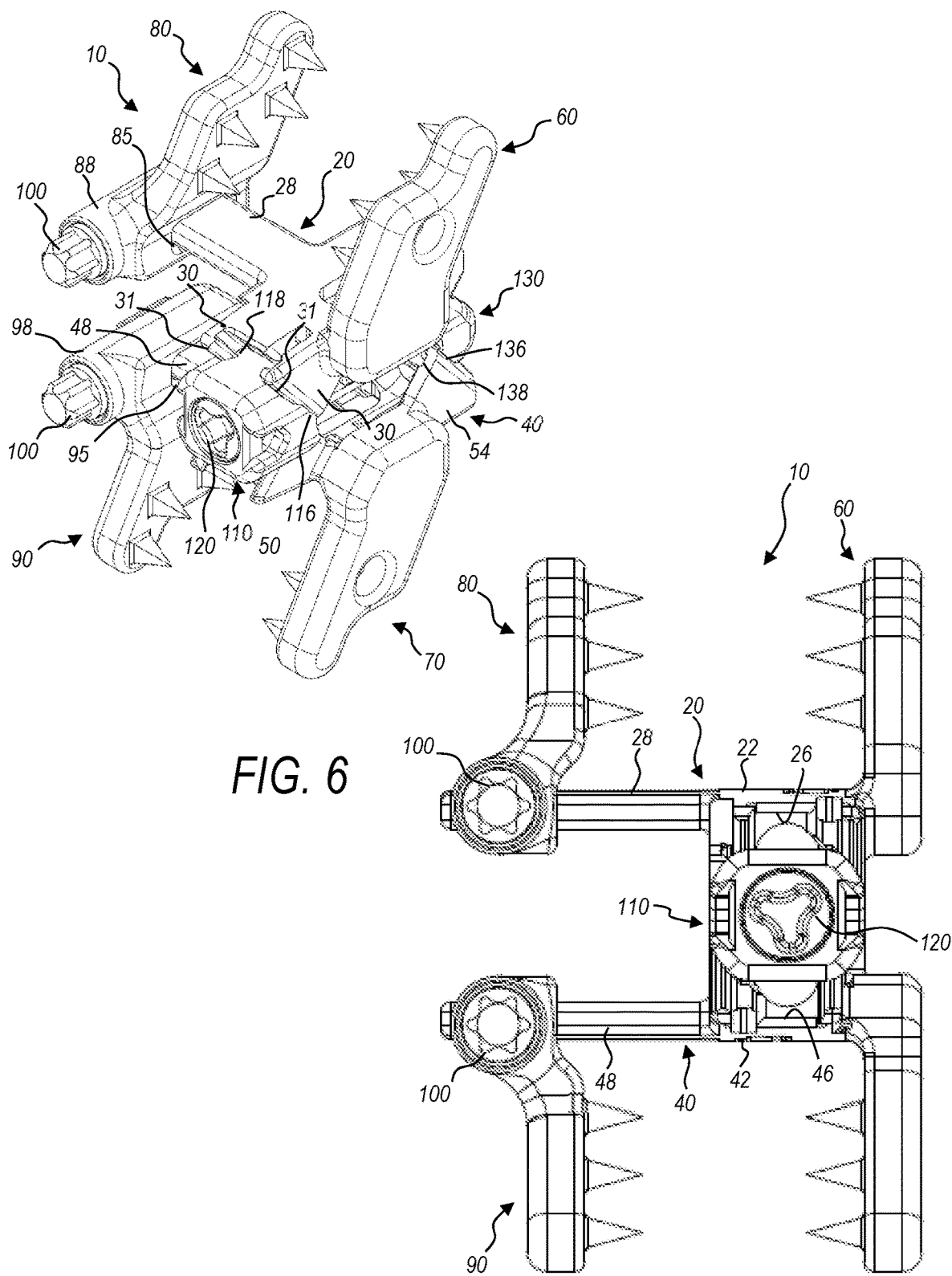

EXPANDABLE INTERSPINOUS PROCESS FIXATION DEVICE

CROSS REFERENCE TO RELATED APPLICATIONS

This application is a continuation application of U.S. patent application Ser. No. 15/920,708 filed on Mar. 14, 2018 (published as U.S. Pat. Pub. No. 2018-0263784), which is a continuation-in-part of U.S. patent application Ser. No. 15/662,423 filed on Jul. 28, 2017, now U.S. Pat. No. 10,512,550, which is a continuation-in-part of U.S. application Ser. No. 15/635,267, filed Jun. 28, 2017, now U.S. Pat. No. 10,842,644, which is a continuation-in-part of U.S. application Ser. No. 15/189,188, filed Jun. 22, 2016, now U.S. Pat. No. 10,085,849, which is a continuation-in-part of U.S. application Ser. No. 15/014,189, filed Feb. 3, 2016, now U.S. Pat. No. 9,907,673, which is a continuation-in-part of U.S. application Ser. No. 14/109,429, filed Dec. 17, 2013, now U.S. Pat. No. 9,370,434, which is a divisional of U.S. patent application Ser. No. 12/875,818, filed Sep. 3, 2010, now U.S. Pat. No. 8,632,595, the entire disclosures of which are incorporated herein by reference in their entireties for all purposes.

FIELD OF THE INVENTION

The present disclosure is generally directed to surgical devices, systems, and methods. More particularly, the present disclosure is directed to expandable interspinous process fixation devices, systems, and methods.

BACKGROUND

A spine comprises vertebrae which are a series of small bones, and also includes spinous processes. A spinous process is one of two bony protrusions arising from the posterior side of each vertebra in the human spine. Extending backwards and downwards from the main body of the vertebra, each spinous process is an extension of the lamina. The laminae are two bony plates that converge at the back of each vertebra to form the vertebral arch. The spinous processes curve outward from this junction. A variety of scenarios may exist where damage to the spine may occur including, but not limited to, injury or illness. Severe, even debilitating, pain can result from such damage. In some instances, artificial assistance may be necessary to address such damage.

Surgical procedures exist that attempt to address such damage including using various vertebral fixation devices. Conventional devices exist to implant vertebrae fixation devices, but such devices often suffer from the problem of being purely manual and are usually complex. Such manual devices require the use of human muscle, which can fatigue, to perform the procedure. Moreover, the incision opening for insertion of these fixation devices may require substantial openings to achieve access to the spinous process.

There are drawbacks associated with the known conventional fixation devices and methodologies. For example, present methods for installing a conventional fixation device often require that the adjacent vertebral bodies be distracted to restore a diseased disc space to its normal or healthy height prior to implantation of the fixation device. In order to maintain this height once the fixation device is inserted, the fixation device is usually dimensioned larger in height than the initial distraction height. This difference in height can make it difficult for a surgeon to install the fixation device in the distracted intervertebral space.

As such, there exists a need for a fixation device capable of being installed inside an intervertebral disc space at a minimum to no distraction height and for a fixation device that can maintain a normal distance between adjacent vertebral bodies when implanted.

SUMMARY

To meet this and other needs, devices, systems, and methods of fixation are provided. The fixation devices and systems may include expandable interspinous process fixation devices and system and associated method of implantation.

In at least one embodiment, the present disclosure provides an expandable interspinous process fixation system which is a posterior, non-pedicle supplemental fixation device. In some embodiments, the interspinous process fixations system may be intended for use in the non-cervical spine. The interspinous process fixations system may attach firmly to adjacent spinous processes and immobilize a lumbar motion segment posteriorly. The device may be configured to withstand compressive, torsional, and shear loads seen in the lumbar spine. The device is intended to achieve supplemental fusion, treating various conditions, for example, degenerative disc disease; spondylolisthesis; trauma (i.e., fracture or dislocation); tumor; and/or other conditions.

In at least one embodiment, a device according to the present disclosure allows for insertion of a spinous process fixation implant at a reduced height and then an increase of the height after insertion to achieve an accurate anatomical fit. Adjustability of the implant greatly reduces the complexity of inserting an interspinous device since one device covers a wide range of implant sizes, negating the need for several variations of implant lengths and widths. The implant may be preassembled, greatly reducing the number of steps required to insert the device, which simplifies the overall procedure and reduces operating room time.

In at least one embodiment, the present disclosure provides a fixation device including first and second endplates for an intervertebral implant. The first endplate has a first lateral adjustment arm extending from a first edge thereof and the second endplate has a second lateral adjustment arm extending from a first edge thereof. A first fixed plate extends along a second edge of the first endplate opposite the first edge thereof. The first fixed plate extends substantially perpendicular to the first endplate and has an inner surface defining a first spinous process engaging surface. A second fixed plate extends along a second edge of the second endplate opposite the first edge thereof. The second fixed plate extends substantially perpendicular to the second endplate and has an inner surface defining a second spinous process engaging surface. A first sliding plate is adjustably mounted on the first lateral adjustment arm such that the first sliding plate extends substantially perpendicular to the first endplate and has an inner surface defining a third spinous process engaging surface. A second sliding plate is adjustably mounted on the second lateral adjustment arm such that the second sliding plate extends substantially perpendicular to the second endplate and has an inner surface defining a fourth spinous process engaging surface. An expansion assembly is positioned between the first and second endplates and is configured to selectively cause the first and second endplates to move apart.

In at least one embodiment, the present disclosure provides a method including: inserting an expandable fixation device into an intervertebral disc space, wherein the expandable fixation device includes: a first endplate for an intervertebral implant, the first endplate having a first lateral adjustment arm extending from a first edge thereof; a second endplate for an intervertebral implant, the second endplate having a second lateral adjustment arm extending from a first edge thereof; a first fixed plate extending along a second edge of the first endplate opposite the first edge thereof, the first fixed plate extending substantially perpendicular to the first endplate and having an inner surface defining a first spinous process engaging surface; a second fixed plate extending along a second edge of the second endplate opposite the first edge thereof, the second fixed plate extending substantially perpendicular to the second endplate and having an inner surface defining a second spinous process engaging surface; a first sliding plate adjustably mounted on the first lateral adjustment arm such that the first sliding plate extends substantially perpendicular to the first endplate and has an inner surface defining a third spinous process engaging surface; a second sliding plate adjustably mounted on the second lateral adjustment arm such that the second sliding plate extends substantially perpendicular to the second endplate and has an inner surface defining a fourth spinous process engaging surface; an expansion assembly positioned between the first and second endplates; the expansion assembly configured to selectively cause the first and second endplates to move apart; actuating the expansion assembly to cause movement of the first and the second endplates away from one another; adjusting the lateral position of the first sliding plate such that spinous processes are compressed between the first and third spinous process engaging surfaces and thereafter fixing the position of the first sliding plate; and adjusting the lateral position of the second sliding plate such that spinous processes are compressed between the second and fourth spinous process engaging surfaces and thereafter fixing the position of the second sliding plate.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIG. 6 is a perspective view of the expandable fixation device of FIG. 1 shown in an expanded position;

FIG. 7 is a front elevation view of the expandable fixation device of FIG. 1 in the expanded position;

DETAILED DESCRIPTION

Figure 1:
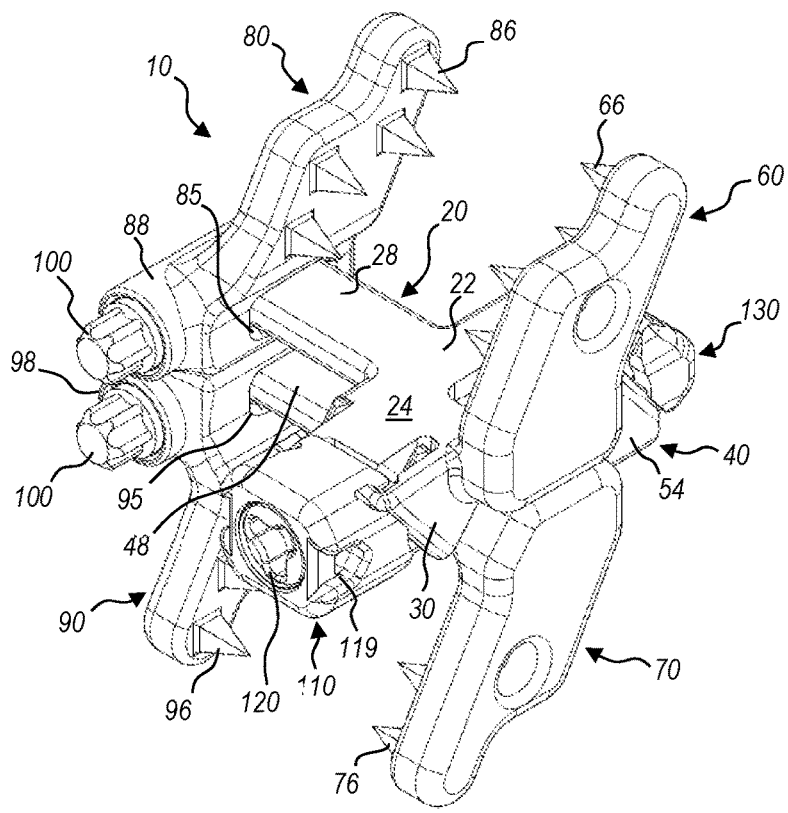
FIG. 1 is a perspective view of the expandable fixation device in accordance with one embodiment of the present disclosure shown in an unexpanded position.
Figure 2:
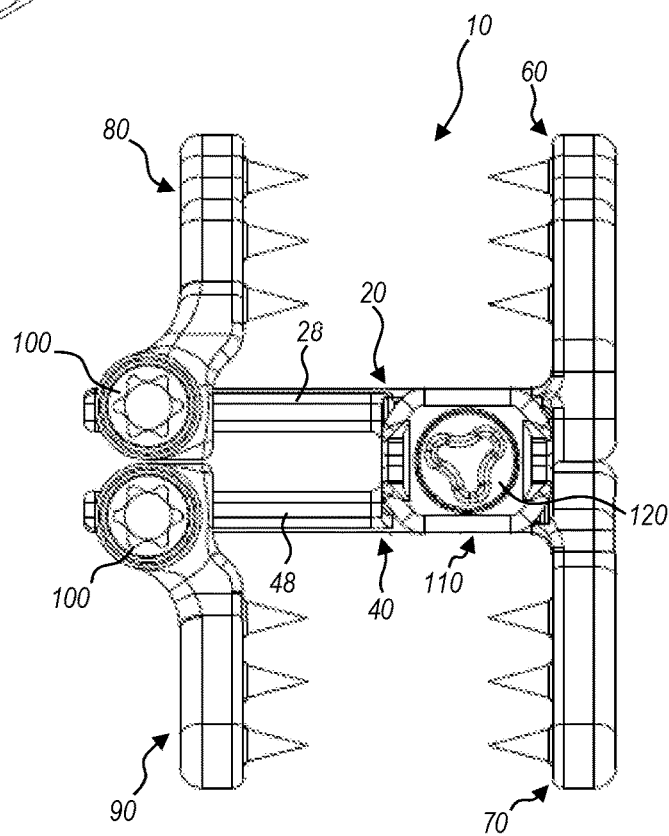
FIG. 2 is a front elevation view of the expandable fixation device of FIG. 1 in the unexpanded position.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

Surgical intervention for back pain may occur for people with chronic back pain, perhaps for which other treatments have failed. Surgery may be required, for example, for people who have chronic lower back pain and sciatica (often diagnosed with a herniated disc), spinal stenosis, spondylolisthesis (vertebra of the lumbar spine slips out of place), vertebral fractures with nerve involvement, or other indications as assessed by a medical professional. Also, surgery may be necessary for people with discogenic lower back pain (e.g., degenerative disc disease) that may occur as part of the aging process. In these situations, among others, implants may be included in a course of treatment. Generally, the goal may be to achieve supplemental fusion or complete fusion of the spine.

With reference to FIGS. 1-9, an embodiment of the fixation device 10 is shown. In the exemplary embodiment, the fixation device 10 includes a first endplate 20, a second endplate 40, first and second fixed plates 60, 70, a pair of sliding plates 80, 90, a central ramp 110, and a driving ramp 130.

Each of the endplates 20, 40 includes a body 22, 42 extending between opposed ends 21, 23; 41, 43. In the illustrated embodiment, each endplate body 22, 42 defines an outer surface 24, 44 connecting the first end 21, 41 and the second end 23, 43, and an inner surface 26, 46 connecting the first end 21, 41 and the second end 23, 43. In an embodiment, each endplate 20, 40 defines a through opening 25, 45. The through openings 25, 45, in an exemplary embodiment, are sized to receive bone graft or similar bone growth inducing material and further allow the bone graft or similar bone growth inducing material to be packed in a central area of the device 10.

The outer surface 24, 44 of each endplate 20, 40 may be flat and generally planar to allow the outer surface 24, 44 of the endplate 20, 40 to engage with an adjacent vertebral body. Alternatively, one or both of the outer surfaces 24, 44 can be curved convexly or concavely to allow for a greater or lesser degree of engagement with the adjacent vertebral body. It is also contemplated that the outer surfaces 24, 44 can be generally planar but include a generally straight ramped surface or a curved ramped surface, angled, or otherwise configured. The presence of one or more ramped surfaces may allow for engagement with the adjacent vertebral body in a lordotic fashion. While not illustrated, in an exemplary embodiment, one or both outer surfaces 24, 44 may include texturing or other surface features to aid in gripping the adjacent vertebral bodies. Although not limited to the following, the texturing or other surface features can include teeth, ridges, friction increasing elements, keels, gripping or purchasing projections, or the like.

Figure 3:
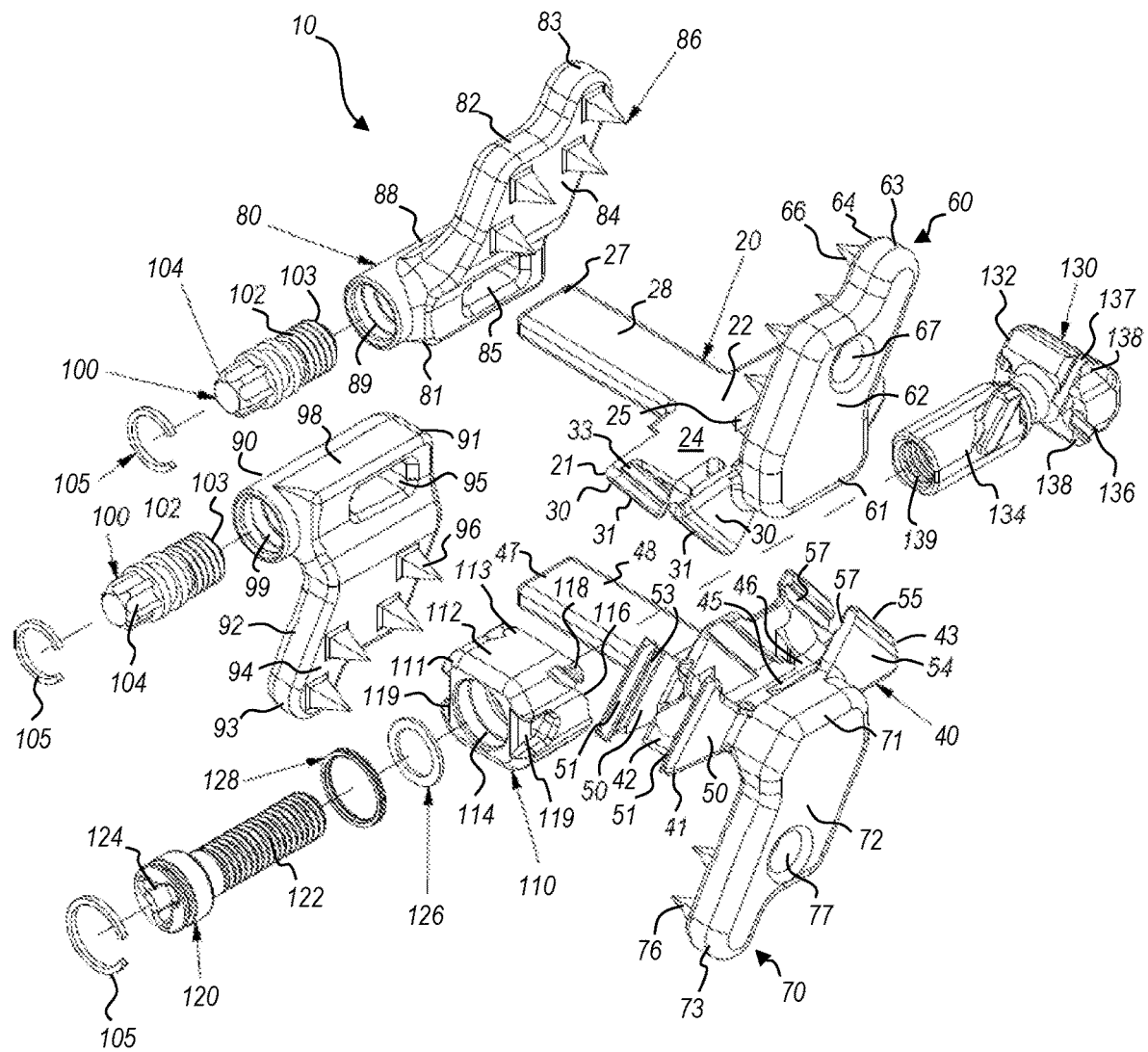
FIG. 3 is an exploded perspective view of the expandable fixation device of FIG. 1.
Figure 4:
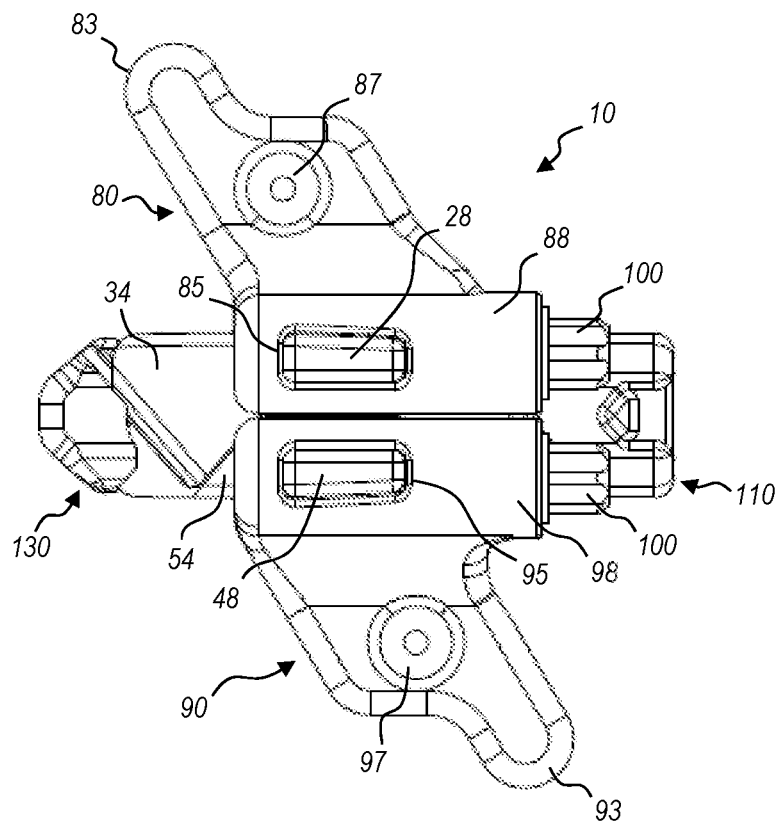
FIG. 4 is a left side view of the expandable fixation device of FIG. 1 in the unexpanded position.
Figure 5:
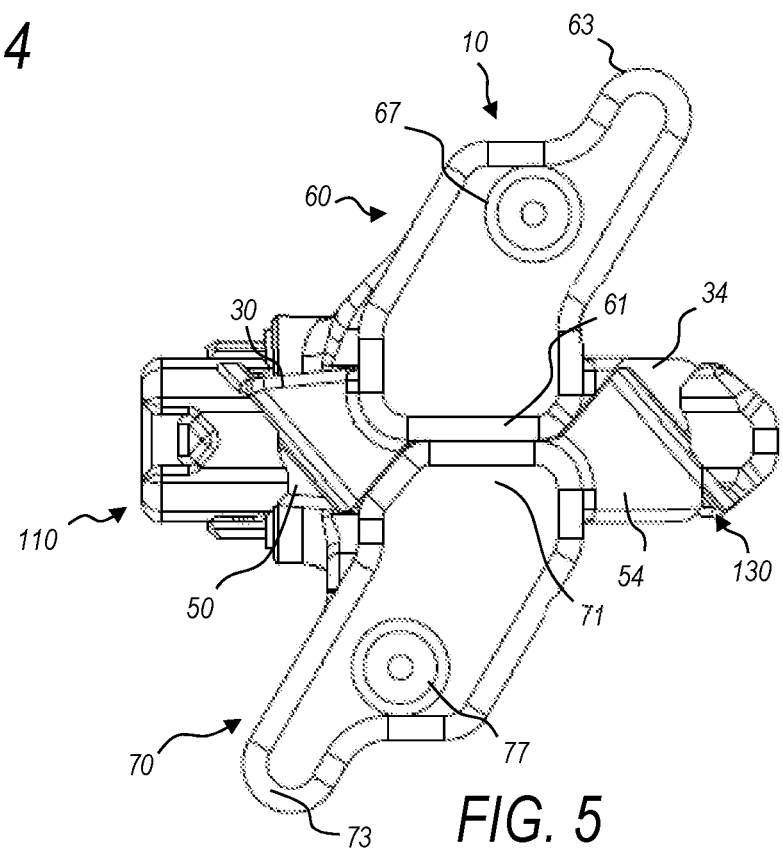
FIG. 5 is a right side view of the expandable fixation device of FIG. 1 in the unexpanded position.
Figure 8:
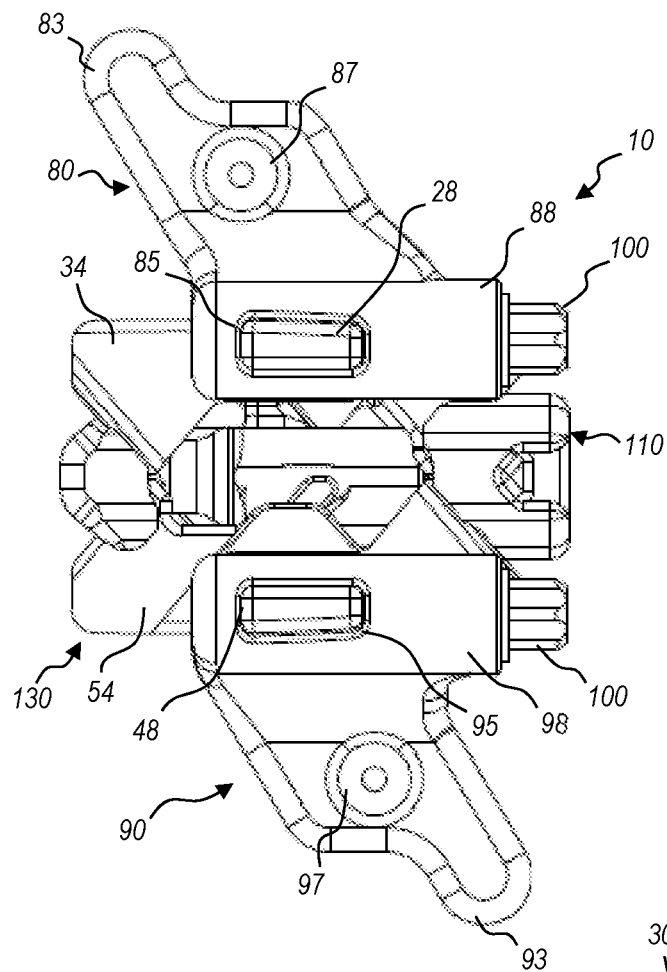
FIG. 8 is a left side view of the expandable fixation device of FIG. 1 in the expanded position.
Figure 9:
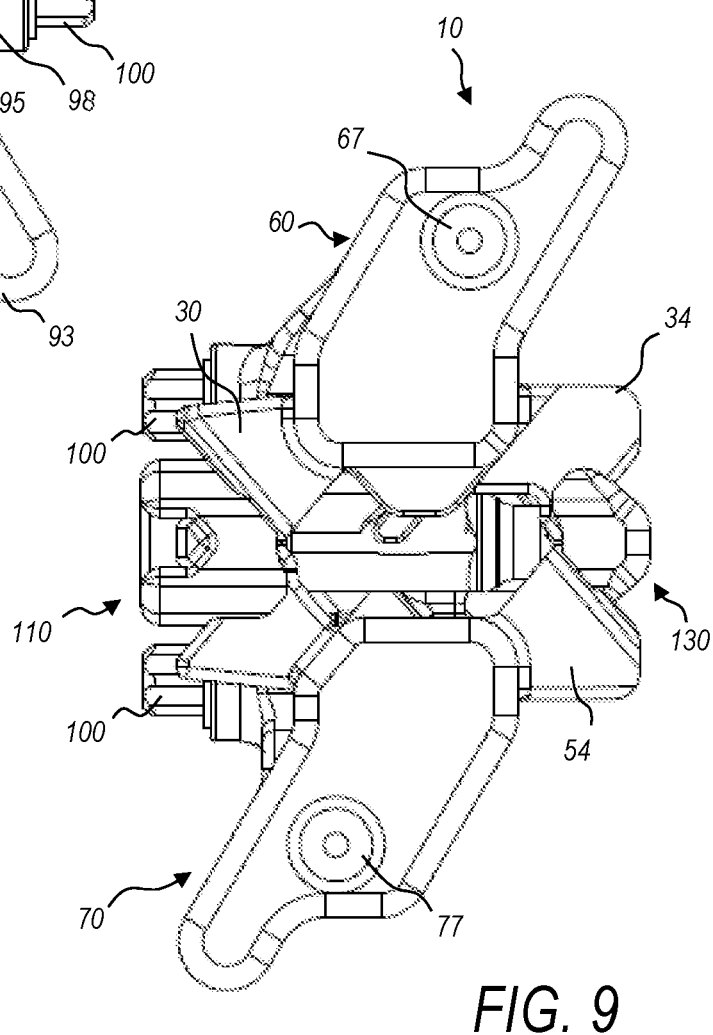
FIG. 9 is a right side view of the expandable fixation device of FIG. 1 in the expanded position.
Figure 10:
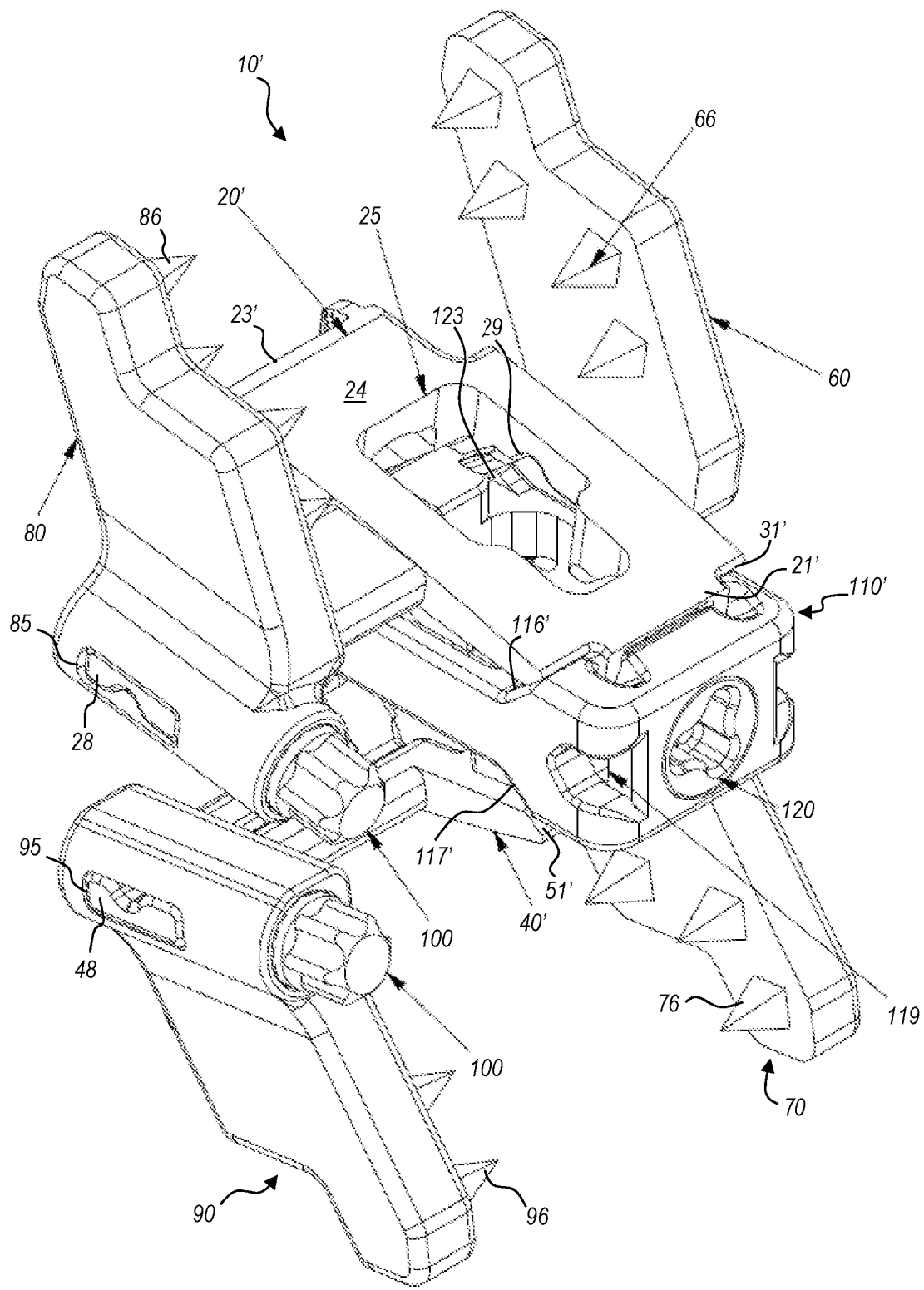
FIG. 10 is a perspective view of the expandable fixation device in accordance with another embodiment of the present disclosure shown in an expanded position.
Figure 11:
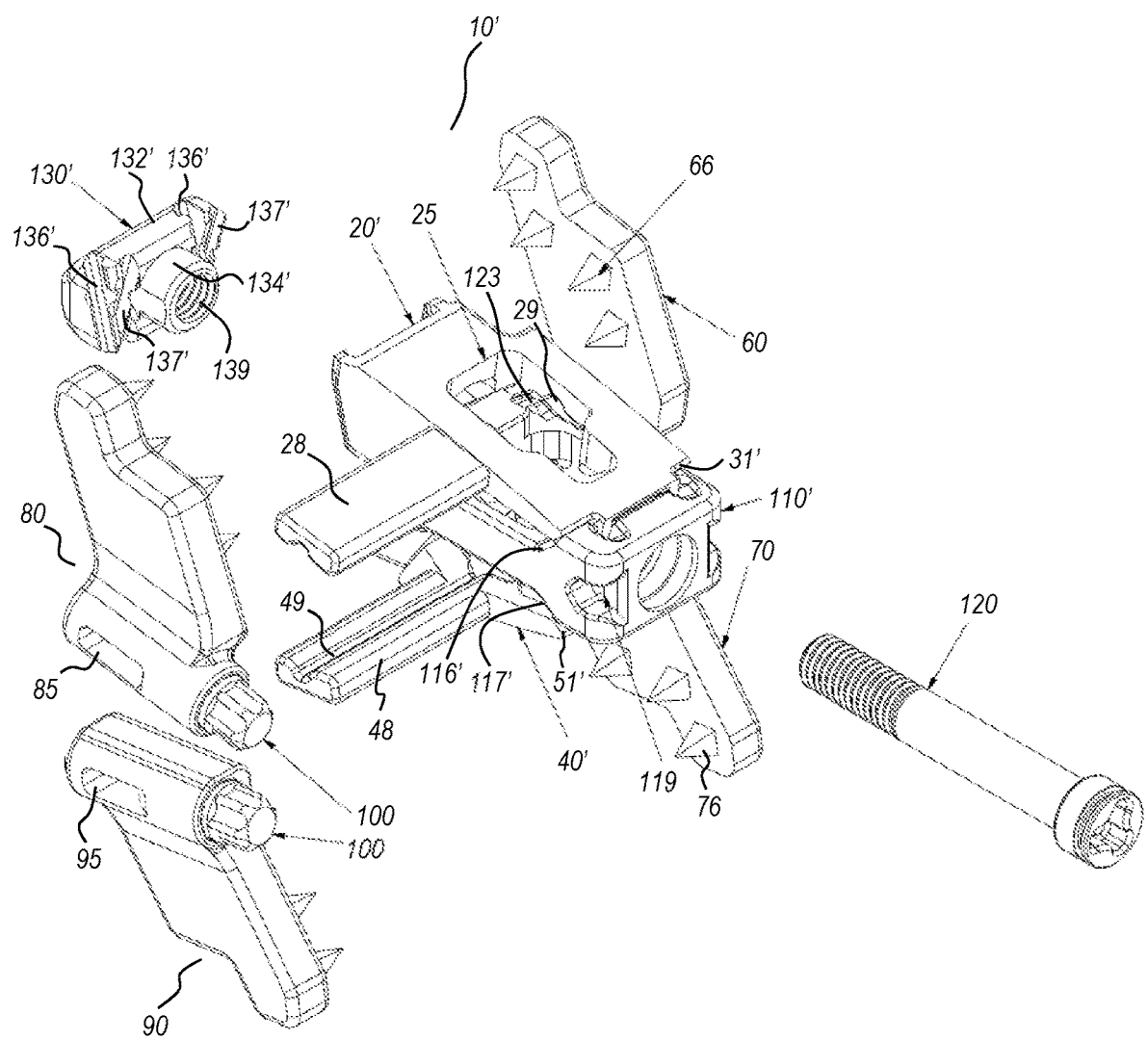
FIG. 11 is an exploded perspective view of the expandable fixation device of FIG. 10.

Referring to FIGS. 3, 5 and 9, the inner surface 26 of the first endplate 20 defines a first pair of spaced apart extensions 30 at the first end 21 of the body 22 and a second pair of spaced apart extensions 34 at the second end 23 of the body. The extensions 30 at the first end 21 are positioned oppositely of the extensions 34 at the second end 23, e.g., on the first end 21, the extension 30 on the right side is at the edge while the extension on the left side is inward of the edge and on the second end 23, the extension 34 on the right side is inward of the edge while the extension on the left side is at the edge. Similarly, the inner surface 46 of the second endplate 40 defines a first pair of spaced apart extensions 50 at the first end 41 of the body 42 and a second pair of spaced apart extensions 54 at the second end 43 of the body. With the second endplate 40, the extensions 50, 54 are opposite of those on the first plate 20 i.e. on the first end 41, the extension 50 on the right side is inward from the edge while the extension on the left side is at the edge and on the second end 43, the extension 54 on the right side is at the edge while the extension on the left side is inward of the edge. With this configuration, the extensions 30 of the first endplate 20 overlap the extensions 50 of the second endplate 40 and the extensions 54 of the second endplate 40 overlap the extensions 34 of the first endplate 20.

Each of the extensions 30, 34, 50, 54 defines a respective ramped surface 31, 35, 51, 55. The ramped surfaces 31, 35, 51, 55 are configured to be engaged by ramped surfaces on the central ramp 110 and the driving ramp 130, as will be described hereinafter. Each of the extensions 30, 34, 50, 54 also defines a respective groove 33, 37, 53, 57. The grooves 33, 37, 53, 57 are configured to be engaged by projections on the central ramp 110 and the driving ramp 130 to maintain the device 10 in an assembled condition and to guide movement of the endplates 20, 40, as will be described hereinafter.

Each endplate 20, 40 includes a fixed plate 60, 70 attached along one side edge of the body 22, 42. Each fixed plate 60, 70 of the illustrated embodiment includes a body 62, 72 extending from a fixed end 61, 71 to a free end 63, 73. The fixed plate bodies 62, 72 may have any desired shape to complement the intended engagement with respective spinous processes, and may be mirror images of one another or may be distinct from one another. The inner surface 64, 74 of each fixed plate 60, 70 includes a plurality of spikes 66, 76 or the like to grip the spinous processes when engaged therewith. The outer surface of each fixed plate may include a blind bore 67, 77, through bore or the like. The bores 67, 77, in an exemplary embodiment, are sized to receive bone graft or similar bone growth inducing material.

A lateral adjustment bar 28, 48 extends outwardly from the opposite side edge of the body 22, 42 of each end plate 20, 40 to a free end 29, 49. The adjustment bars 28, 48 support respective sliding plates 80, 90. Each sliding plate 80, 90 of the illustrated embodiment includes a body 82, 92 extending from a connection end 81, 91 to a free end 83, 93. The sliding plate bodies 82, 92 may have any desired shape to complement the intended engagement with respective spinous processes, and may be mirror images of one another or may be distinct from one another. The inner surface 84, 94 of each fixed plate 80, 90 includes a plurality of spikes 86, 96 or the like to grip the spinous processes when engaged therewith. The outer surface of each fixed plate may include a blind bore 87, 97, through bore or the like. The bores 87, 97, in an exemplary embodiment, are sized to receive bone graft or similar bone growth inducing material.

The connection end 81, 91 of each sliding plate 80, 90 includes a connection assembly 88, 98 which allows the sliding plate 80, 90 to be mounted on a respective lateral adjustment bar 28, 48 such that the sliding plate 80, 90 is laterally adjustable but rotationally fixed. In the illustrated embodiment, each connection assembly 88, 98 defines a receiving bore 85, 95 extending laterally through the body 82, 92 and configured to receive the respective lateral adjustment bar 28, 48. The receiving bores 85, 95 and the lateral adjustment bars 28, 48 have complementary shapes which allow lateral adjustment but prevent relative rotation. In the illustrated embodiment, the receiving bores 85, 95 and lateral adjustment bars 28, 48 have complementary rounded rectangle shapes, but other non-circular shapes are possible.

To set the position of the sliding plate 80, 90 along the respective lateral adjustment bar 28, 48, a set screw 100 extends into a through bore 89, 99 defined in the respective connection assembly 88, 98 and intersects with the receiving bore 85, 95. Each set screw 100 includes a threaded portion 102 and a driving head 104 with an engagement end 103 extending toward the receiving bore 85, 95. The threaded portion 102 is configured to engage threads within the through bore 89, 99. A retaining ring 105 or the like may be positioned about each set screw 100 and engage a groove within the through bore 89, 99 to retain the set screw 100 with the through bore 89, 99 after assembly. Once the sliding plate 80, 90 is positioned at a desired lateral position along the respective lateral adjustment bar 28, 48, the set screw 100 is threadably advanced such that the engagement end 103 engages the lateral adjustment bar 28, 48 and fixes the sliding plate 80, 90 relative to the respective endplate 20, 40.

The central ramp 110 includes a body 112 extending from a first end 111 to a second end 113. A through bore 114 extends through the body 112 from the first end 111 to the second end 113 and is configured to receive a drive screw 120 therethrough. The drive screw 120 has a threaded portion 122 and drive head 124. A flat washer 126 and a drag reducing washer 128 may be positioned within the through bore 114 between the drive head 124 and an internal shoulder defined within the through bore 114 (not show) to facilitate driving of the central ramp while minimizing drag. Notches 119 or the like may be defined along the central ramp body 112 configured for engagement with a delivery/positioning tool (not shown) or the like.

The second end 113 of the central ramp 110 defines a first pair of ramps 116 and a second pair of ramps 117. The first ramps 116 are aligned with and configured to slidably engage the ramps 31 on the first endplate 20. The second ramps 117 are aligned with and configured to engage the ramps 51 on the second end plate 40. Projections 118 adjacent the ramps 116 extend into the grooves 33 on the first endplate 20 while projection adjacent to the ramps 117 (not shown) extend into the grooves 53 on the second endplate 40. Engagement between the projections 118 and grooves 33, 53 maintains the central ramp 110 assembled to the endplates 20, 40 and guides movement of the endplates 20, 40 as the central ramp 110 is advanced.

The driving ramp 130 includes a ramp body 132 and a screw receiving portion 134. A threaded blind bore 139 extends into the screw receiving portion 134 and is configured to receive the threaded portion 122 of the drive screw 120. As such, rotation of the drive screw 120 in the advancement direction causes the central ramp 110 and the driving ramp 130 to move toward one another.

The ramp body 132 of the driving ramp 130 defines a pair of first ramps 136 and a pair of second ramps 137 (see FIG. 3). The first ramps 136 are aligned with and configured to slidably engage the ramps 55 on the second endplate 40. The second ramps 137 are aligned with and configured to engage the ramps 35 on the first end plate 20. Projections 138 adjacent the ramps 136 extend into the grooves 57 on the second endplate 40 while projections 138 adjacent to the ramps 137 extend into the grooves 37 on the first endplate 20. Engagement between the projections 138 and grooves 37, 57 maintains the driving ramp 130 assembled to the endplates 20, 40 and guides movement of the endplates 20, 40 as the driving ramp 130 is advanced.

Having generally described the components of the fixation device 10, operation thereof will generally be described. The fixation device 10 may be inserted at its fully collapsed height as illustrated in FIGS. 1, 2, 4 and 5 to allow for easy insertion into a collapsed interspinous space. During insertion, the spikes 66, 76 of the fixed plates 60, 70 may be compressed into the respective spinous processes. After insertion, the fixation device 10 may be expanded by rotating the drive screw 120 in an advancement direction. As the drive screw 120 is rotated, the central ramp 110 and driving ramp 130 are drawn toward one another, with the ramps 31 riding up the ramps 116, the ramps 51 riding up the ramps 117, the ramps 35 riding up the ramps 137, the ramps 55 riding up the ramps 136. Such movement causes the endplates 20, 40 to move away from one another, thereby increasing the height of the fixation device 10 to get the desired fit, or used to distract the interspinous space to relieve pressure on neurological elements. As the endplates 20, 40 move away from one another, the fixed plates 60, 70 and sliding plates 80, 90 move in conformity therewith. After expansion of the endplates 20, 40, the sliding plates 80, 90 are moved along the lateral adjustment bars 28, 48 and compressed onto the spinous processes. Once positioned, the sliding plates 80, 90 are locked into position using the set screws 100.

Referring to FIGS. 10-16, another embodiment of the fixation device 10' is shown. The fixation device 10' of the present exemplary embodiment is similar to the fixation device 10 of the previous embodiment and includes a first endplate 20', a second endplate 40', first and second fixed plates 60, 70, a pair of sliding plates 80, 90, a central ramp 110', and a driving ramp 130'. Only the differences between the embodiments will be described. Otherwise, the fixation devices 10, 10' operate is substantially the same manner.

Figure 14:
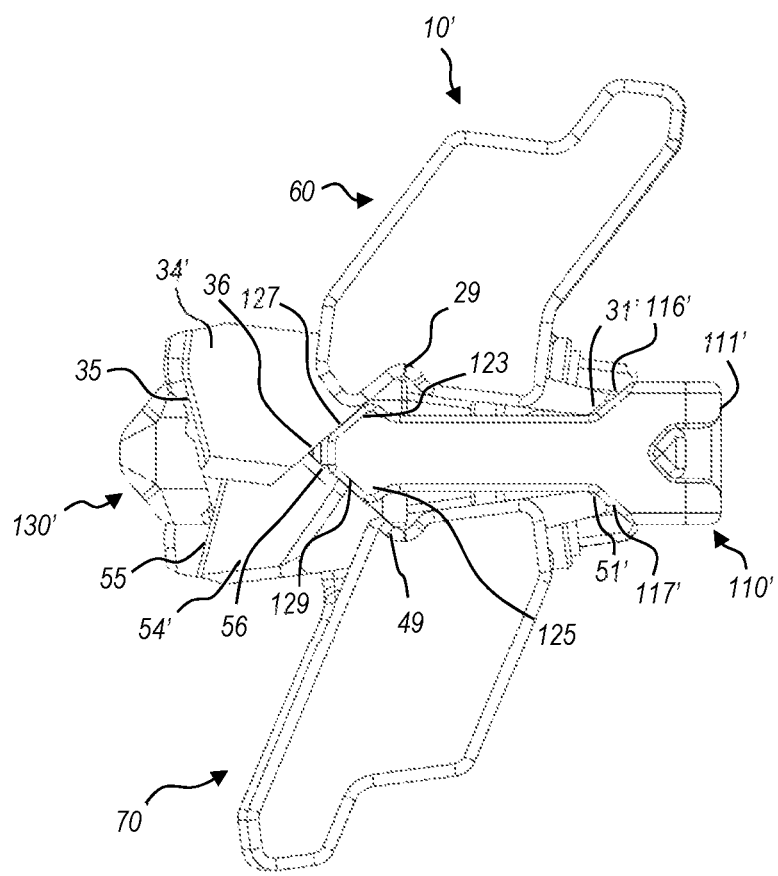
FIG. 14 is a right side view of the expandable fixation device of FIG. 10 in an intermediate position.

In the present embodiment, the endplates 20' and 40' and the central ramp 110' are configured to cause pivoting between the endplates 20', 40' prior to expansion thereof. As in the previous embodiment, each endplate 20', 40' includes a body 22', 42' extending from a first end 21', 41' to a second end 23', 43'. Referring to FIG. 14, in the present embodiment, the first ends 21', 31' do not include extensions, but instead have a tapered end surface which defines the ramps 31' 51'. The second ends 23', 43' are similar to the previous embodiment and include extensions 34', 54' defining the ramps 35, 55. The extensions 34' 54' also define inward ramps 36, 56. Inward of the extensions 34, 54, each endplate body 22', 44' defines a retaining notch 29, 49. The retaining notches 29, 49 are configured to be engaged by an inward end 113' of the central ramp 110' and prevent inward advancement of the central ramp 110' until the endplates 20' 40' have pivoted relative to one another.

The central ramp 110' includes a body 112' extending from a first end 111' to a second end 113' with the body 112' having a longer length compared to the central ramp body 112 of the previous embodiment. A through bore 114 extends through the body 112' from the first end 111' and is configured to receive the drive screw 120 therethrough. The first end 111' of the central body 110' defines ramps 116' and 117'. The ramps 116' and 117' are configured to engage the ramps 31' and 51', respectively.

The second end 113' of the central ramp 110 defines a pair of extensions 123 on a first surface thereof and a pair of extensions 125 on the opposite surface. The extensions 123 are aligned with and configured to be received in the notches 29 defined by the first endplate 20' and the extensions 125 are aligned with and configured to be received in the notches 49 defined by the second endplate 40' (see FIG. 13). The extensions 123 also define forward ramps 127 while the extensions 125 define forward ramps 129.

The driving ramp 130' includes a ramp body 132' and a screw receiving portion 134'. The screw receiving portion 134' is shorter in length than in the previous embodiment. A threaded blind bore 139 extends into the screw receiving portion 134' and is configured to receive the threaded portion 122 of the drive screw 120.

The ramp body 132' of the driving ramp 130' defines a pair of ramps 136' aligned with and configured to slidably engage the ramps 55 on the second endplate 40'. The ramp body 132' also defines a pair of ramps 137' which are aligned with and configured to engage the ramps 35 on the first end plate 20'. Projections 138' adjacent the ramps 136', 137' extend into the grooves 37, 57 on the endplates 20', 40'. Engagement between the projections 138' and grooves 37, 57 maintains the driving ramp 130' assembled to the endplates 20', 40' and guides movement of the endplates 20', 40' as the driving ramp 130' is advanced.

Figure 12:
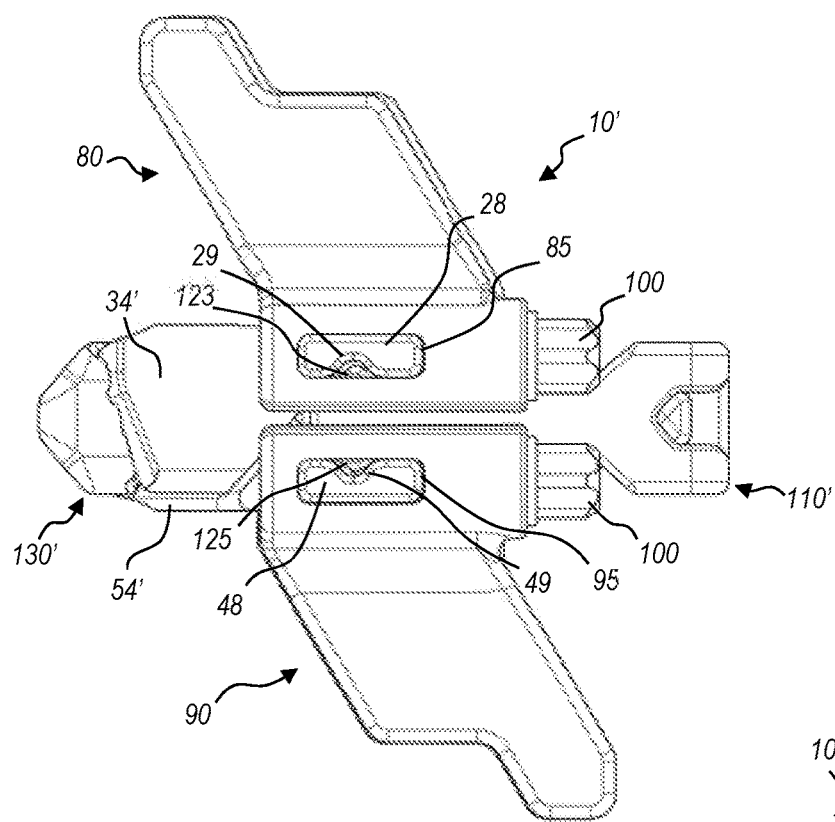
FIG. 12 is a left side view of the expandable fixation device of FIG. 10 in an unexpanded position.
Figure 13:
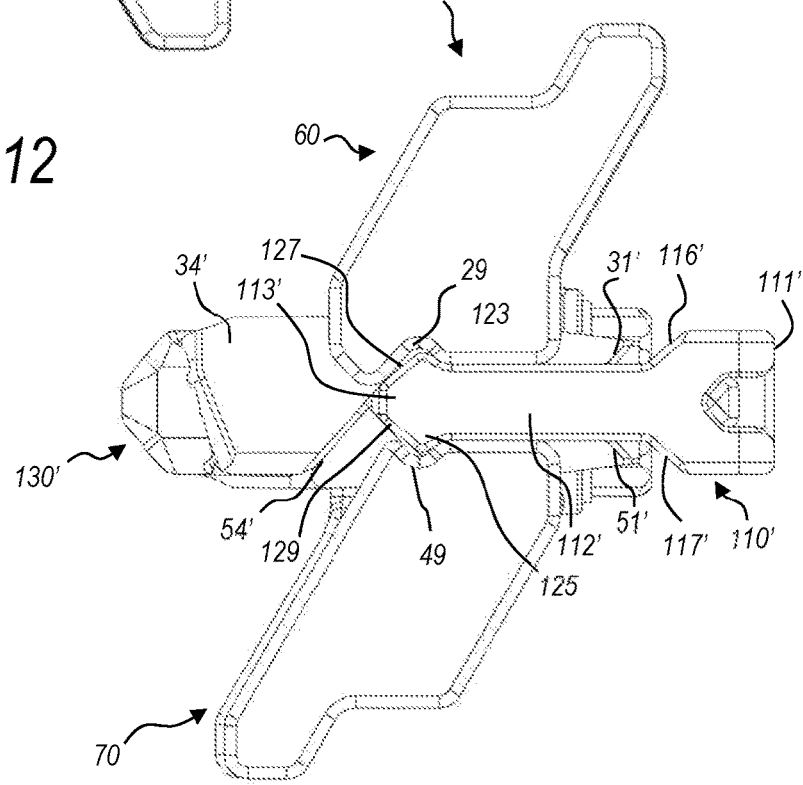
FIG. 13 is a right side view of the expandable fixation device of FIG. 10 in the unexpanded position.
Figure 15:
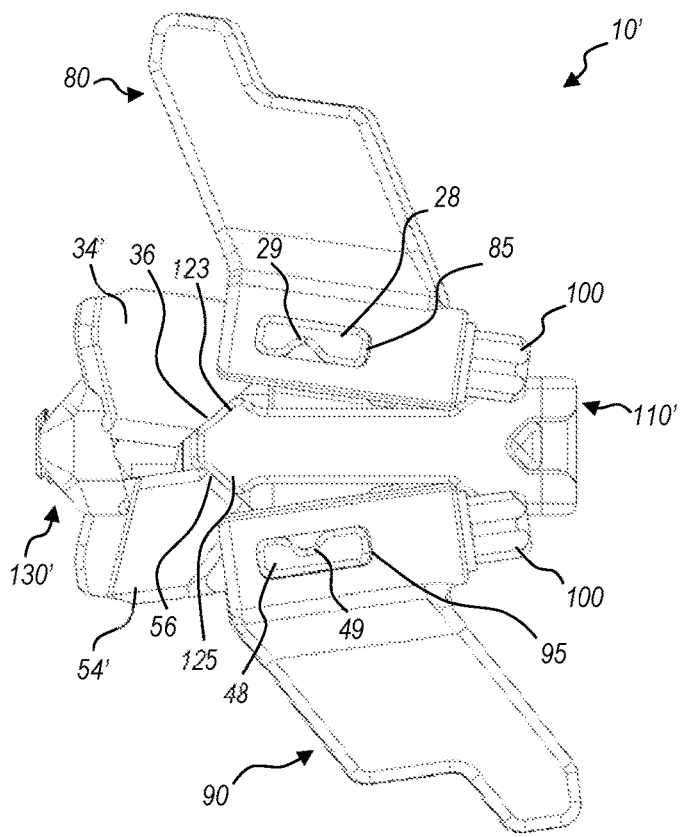
FIG. 15 is a left side view of the expandable fixation device of FIG. 10 in the expanded position.
Figure 16:
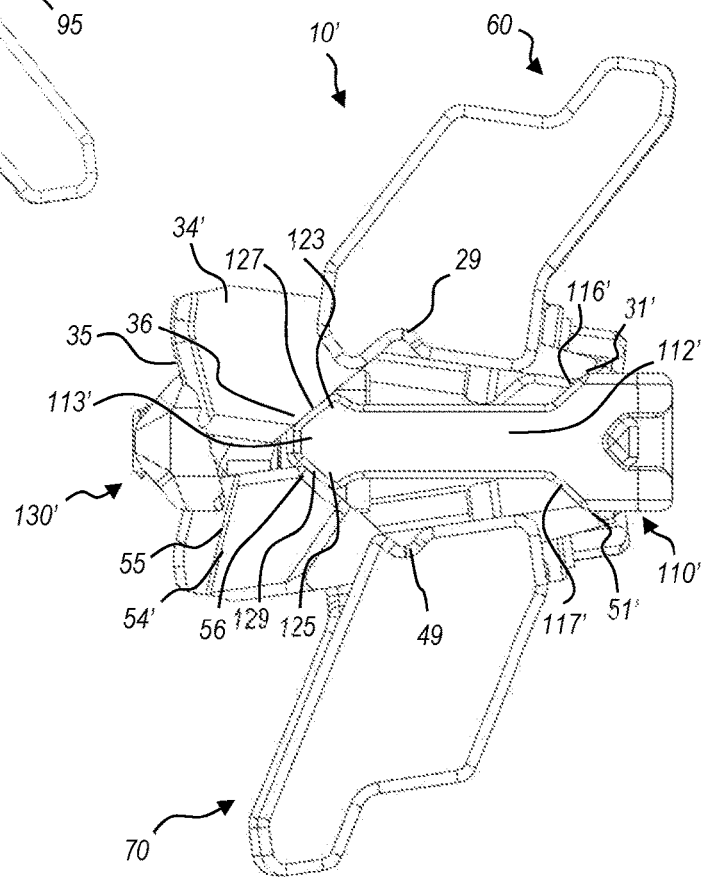
FIG. 16 is a right side view of the expandable fixation device of FIG. 10 in the expanded position.

Having generally described the components of the fixation device 10', operation thereof will generally be described with reference to FIGS. 12-16. The fixation device 10' may be inserted at its fully collapsed height as illustrated in FIGS. 12 and 13 to allow for easy insertion into a collapsed interspinous space. As illustrated, in the collapsed position, the extensions 123 and 125 are positioned in the respective notches 29, 49. During insertion, the spikes 66, 76 of the fixed plates 60, 70 may be compressed into the respective spinous processes. After insertion, the angular relation between the endplates 20', 40' is adjusted by rotating the drive screw 120 in an advancement direction. During initial advancement of the drive screw 120, engagement of the extensions 123, 125 in the notches 29, 49 prevents the central ramp 110' from advancing. Only the driving ramp 130' is able to advance. As the driving ramp 130' advances, the ramps 35 ride up the ramps 136' and the ramps 55 ride up the ramps 137'. As illustrated in FIG. 14, such causes the endplates 20', 40' to pivot relative to one another with the ends 23' and 43' moving away from one another. Once the endplates 20', 40' have pivoted a maximum amount (FIG. 14), the extensions 123, 125 are clear of the notches 29, 49. As such, with continued rotational advancement of drive screw 120, the central ramp 110' is free to move toward the driving ramp 130', with the central ramp 110' and the driving ramp 130' drawn to one another, with the ramps 31' riding up the ramps 116', the ramps 51' riding up the ramps 117', the ramps 35 riding up the ramps 136', the ramps 55 riding up the ramps 137', and the forward ramps 127, 129 riding along the inward ramps 36, 56, as illustrated in FIGS. 15 and 16. Such movement causes the endplates 20', 40' to move away from one another, thereby increasing the height of the fixation device 10 to get the desired fit, or used to distract the interspinous space to relieve pressure on neurological elements. As the endplates 20', 40' pivot and then move away from one another, the fixed plates 60, 70 and sliding plates 80, 90 move in conformity therewith. After expansion of the endplates 20', 40', the sliding plates 80, 90 are moved along the lateral adjustment bars 28, 48 and compressed onto the spinous processes. Once positioned, the sliding plates 80, 90 are locked into position using the set screws 100.

The expandable fixation devices 10, 10' may be manufactured from a number of suitable biocompatible materials including, but not limited to, titanium, stainless steel, titanium alloys, non-titanium metallic alloys, polymeric materials, plastics, plastic composites, PEEK, ceramic, elastic materials, or other suitable biocompatible materials.

In an exemplary embodiment, bone graft or similar bone growth inducing material can be introduced around and/or within the fixation device 10, 10' to further promote and facilitate the intervertebral fusion. The fixation device 10, 10', in one embodiment, is preferably packed with bone graft or similar bone growth inducing material to promote the growth of bone through and around the fixation device. Such bone graft may be packed between the endplates of the adjacent vertebral bodies prior to, subsequent to, or during implantation of the fixation device.

Figure 17:
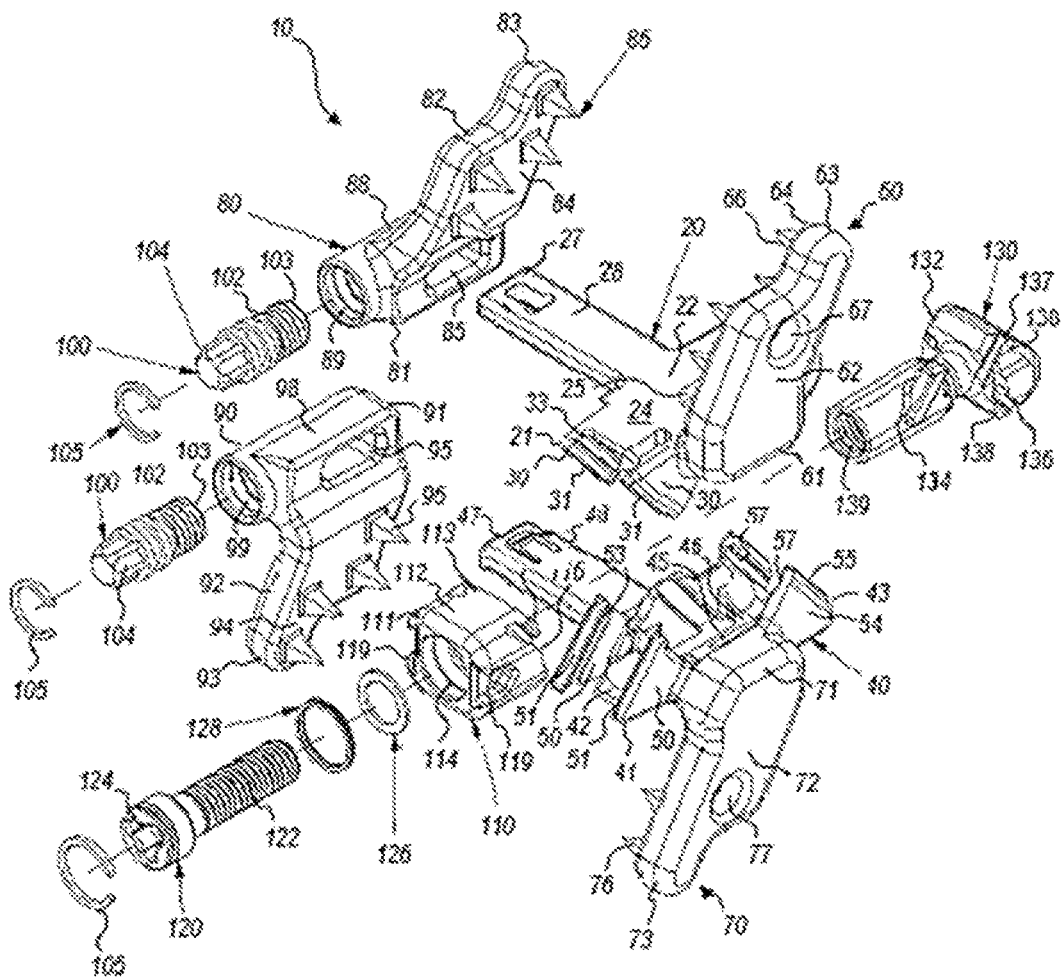
FIG. 17 is an exploded view of an expandable implant in accordance with another embodiment.

Now turning to FIG. 17, yet another embodiment of the expandable implant is disclosed. Each endplate 20, 40 includes a lateral adjustment bar 28, 48 that extends from the body of each endplate 20, 40. The lateral adjustment bar 28, 48 includes a proximal portion and a distal portion, the distal portion includes a retaining features 151, 152 for retaining the sliding plates 80, 90, respectively. The lateral adjustment bar 28, 48 allows for linear translation of the independent sliding plates 80, 90. The retaining features 151, 152 are configured as leaf springs to keep the sliding plates 80, 90 from disengaging from the implant assembly during shipping. The retaining features 151, 152 further include a ramp element 153 that is located at the deflecting end of the leaf spring. The sliding plates 80, 90 have a corresponding slot or opening 85, 95 that mates with the ramp element 153 of the retaining feature and allows for the sliding plates 80, 90 to be moved in only one direction. The ramp element 152 abuts against sliding plates 80, 90 if the sliding plates 80, 90 is moved in a direction to disengage the sliding plates from the lateral adjustment bar. When the plates are compressed, the ramp element allows the leaf spring to depress allowing the surgeon to move the sliding plates 80, 90 on the lateral adjustment bar 28, 48 to clamp the expandable implant to the spinous process.

In other embodiments, different mechanisms to retain the sliding plates to the lateral adjustment bar may be utilized. For example, in one embodiment, a ratcheting type mechanism may be used. In another embodiment, a dovetail connection may be used to retain the sliding plates to the lateral adjustment bar.

Some advantages of the devices described in this disclosure are the ability to insert a spinous process fusion implant at a reduced height and then increase the height after insertion to achieve an accurate anatomical fit. Since the size of the implant is adjustable, it also greatly reduces the complexity of inserting an interspinous device since one device covers a wide range of implant sizes, negating the need for several variations of implant lengths and widths. The implant may be preassembled, greatly reducing the number of steps required to insert the device, which simplifies the overall procedure and reduces operating room time.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A method, comprising:
   inserting an expandable fixation device into an intervertebral disc space, wherein the expandable fixation device comprises:
   a first endplate for an intervertebral implant, wherein the first endplate comprises a first plate portion having a first upper surface and a first lower surface, wherein the first endplate further comprises first front ramped portions extending away from the first lower surface and first rear ramped portions extending away from the first lower surface, the first endplate having a first lateral adjustment arm extending from a first edge thereof;
   a second endplate for an intervertebral implant, wherein the second endplate comprises a second plate portion having a second upper surface and a second lower surface, wherein the second endplate further comprises second front ramped portions extending away from the second lower surface and second rear ramped portions extending away from the second lower surface, the second endplate having a second lateral adjustment arm extending from a first edge thereof;
   a first fixed plate extending along a second edge of the first endplate opposite the first edge thereof, the first fixed plate extending substantially perpendicular to the first endplate and having an inner surface defining a first spinous process engaging surface;

a second fixed plate extending along a second edge of the second endplate opposite the first edge thereof, the second fixed plate extending substantially perpendicular to the second endplate and having an inner surface defining a second spinous process engaging surface;

a first sliding plate adjustably mounted on the first lateral adjustment arm such that the first sliding plate extends substantially perpendicular to the first endplate and has an inner surface defining a third spinous process engaging surface;

a second sliding plate adjustably mounted on the second lateral adjustment arm such that the second sliding plate extends substantially perpendicular to the second endplate and has an inner surface defining a fourth spinous process engaging surface;

a central ramp positioned between the first endplate and the second endplate, wherein the body of the central ramp comprises rear endplate engaging ramps; and a driving ramp positioned between the first endplate and the second endplate, wherein the driving ramp comprises front endplate engaging ramps;

wherein the device is configured such that movement of the central ramp and the driving ramp toward one another causes the first and second endplates to move apart, wherein the first lateral adjustment arm and the second lateral adjustment arm includes a first retaining element and a second retaining element, and wherein the first retaining element and the second retaining elements engage with the first and second sliding plates, respectively, actuating the central ramp and the driving ramp to cause movement of the first and the second endplates away from one another;

adjusting the lateral position of the first sliding plate such that spinous processes are compressed between the first and third spinous process engaging surfaces and thereafter fixing the position of the first sliding plate; and adjusting the lateral position of the second sliding plate such that spinous processes are compressed between the second and fourth spinous process engaging surfaces and thereafter fixing the position of the second sliding plate.

2. The method of claim 1, wherein each spinous process engaging surface has a plurality of spikes extending therefrom.

3. The method of claim 1, wherein each sliding plate has a receiving bore configured to slidably receive a respective lateral adjustment arm.

4. The method of claim 3, wherein each receiving bore and corresponding lateral adjustment arm have complementary shapes such that the respective sliding plate is laterally adjustable but rotationally fixed.

5. The method of claim 1, wherein the first retaining feature and the second retaining feature is a leaf spring.

6. The method of claim 3, wherein each sliding plate includes a through bore in communication with the receiving bore such that a set screw threadably adjustable in the through bore is configured to engage the lateral adjustment arm received in the receiving bore.

7. The method of claim 1, wherein each end endplate has at least one notch adjacent each lateral edge and the central ramp has extensions configured to engage in nothches such that the central ramp is prevented from moving toward the driving ramp until the first and second end plates have pivoted relative to one another.

8. The method of claim 7, wherein a drive screw extends through the central ramp and into threaded engagement with the driving ramp, and wherein, initial forward advancement of the drive screw causes the driving ramp to move toward the central ramp which is prevented from moving, thereby causing the first endplate and the second plate to pivot relative to one another.

9. The method of claim 8, wherein after pivoting of the first and second endplates relative to one another, continued forward advancement of the drive screw causes the central ramp and the driving ramp to move toward one another and the first and second endplates to move apart at a fixed angular relationship.

10. The method of claim 1, wherein the step of fixing the position of the first sliding plate includes advancing a first set screw of the first sliding plate into engagement with the first lateral adjustment arm and the step of fixing the position of the second sliding plate includes advancing a second set screw of the second sliding plate into engagement with the second lateral adjustment arm.

11. A method, comprising:
inserting an expandable fixation device into an intervertebral disc space, wherein the expandable fixation device comprises:
a first endplate for an intervertebral implant, the first endplate having a first lateral adjustment arm extending from a first edge thereof;
a second endplate for an intervertebral implant, the second endplate having a second lateral adjustment arm extending from a first edge thereof;
a first fixed plate extending along a second edge of the first endplate opposite the first edge thereof, the first fixed plate extending substantially perpendicular to the first endplate and having an inner surface defining a first spinous process engaging surface;
a second fixed plate extending along a second edge of the second endplate opposite the first edge thereof, the second fixed plate extending substantially perpendicular to the second endplate and having an inner surface defining a second spinous process engaging surface;
a first sliding plate adjustably mounted on the first lateral adjustment arm such that the first sliding plate extends substantially perpendicular to the first endplate and has an inner surface defining a third spinous process engaging surface;
a second sliding plate adjustably mounted on the second lateral adjustment arm such that the second sliding plate extends substantially perpendicular to the second endplate and has an inner surface defining a fourth spinous process engaging surface;
an expansion assembly positioned between the first and second endplates; the expansion assembly configured to selectively cause the first and second endplates to move apart;
actuating the expansion assembly to cause movement of the first and the second endplates away from one another;
adjusting the lateral position of the first sliding plate such that spinous processes are compressed between the first and third spinous process engaging surfaces and thereafter fixing the position of the first sliding plate; and
adjusting the lateral position of the second sliding plate such that spinous processes are compressed between the second and fourth spinous process engaging surfaces and thereafter fixing the position of the second sliding plate, wherein the first lateral adjustment arm and the second lateral adjustment arm includes a first retaining element and a second retaining element, and wherein the first retaining element and the second retaining elements engage with the first and second sliding plates, respectively.

12. The method of claim 11, wherein each sliding plate has a receiving bore configured to slidably receive a respective lateral adjustment arm.

13. The method of claim 12, wherein each receiving bore and corresponding lateral adjustment arm have complementary shapes such that the respective sliding plate is laterally adjustable but rotationally fixed.

14. The method of claim 13, wherein the first retaining feature and the second retaining feature is a leaf spring.

15. The method of claim 12, wherein each sliding plate includes a through bore in communication with the receiving bore such that a set screw threadably adjustable in the through bore is configured to engage the lateral adjustment arm received in the receiving bore.

16. The method of claim 11, wherein the expansion assembly includes a central ramp and a driving ramp interconnected to one another via a drive screw, the central ramp and the driving ramp each including ramped surfaces configured to engage ramped surfaces on the first and second endplates.

17. The method of claim 16, wherein forward advancement of the drive screw causes the central ramp and the driving ramp to move toward one another, thereby engaging the ramped surfaces and causing the first and second endplates to move away from one another.

18. The method of claim 16, wherein initial forward advancement of the drive screw causes the driving ramp to move toward the central ramp such that the first and second endplates are cause to pivot relative to one another.

19. The method of claim 18, wherein after pivoting of the first and second endplates relative to one another, continued forward advancement of the drive screw causes the central ramp and the driving ramp to move toward one another and the first and second endplates to move apart at a fixed angular relationship.

20. The method of claim 11, wherein the step of fixing the position of the first sliding plate includes advancing a first set screw of the first sliding plate into engagement with the first lateral adjustment arm and the step of fixing the position of the second sliding plate includes advancing a second set screw of the second sliding plate into engagement with the second lateral adjustment arm.

* * * * *